United States Patent [19]
Welch

[11] Patent Number: 5,575,657
[45] Date of Patent: Nov. 19, 1996

[54] HYDRAULIC ENDODONTIA DEVICE

[76] Inventor: Sidney E. Welch, 11132 S. Lowe, Chicago, Ill. 60628

[21] Appl. No.: 498,349

[22] Filed: Jul. 8, 1995

[51] Int. Cl.⁶ .................................................. A61C 5/02
[52] U.S. Cl. ............................................................ 433/224
[58] Field of Search ................................. 433/224, 102, 433/81

[56] References Cited

U.S. PATENT DOCUMENTS

| | | |
|---|---|---|
| 1,067,015 | 7/1913 | Fowler . |
| 1,757,595 | 6/1930 | Siegel ........................................ 433/224 |
| 2,453,696 | 11/1948 | Brooks . |
| 4,518,356 | 5/1985 | Green ........................................ 433/102 |
| 4,740,245 | 4/1988 | Futami et al. ............................ 106/35 |
| 4,824,370 | 4/1989 | Laurichesse et al. ................... 433/102 |
| 5,017,138 | 5/1991 | Schilder ................................... 433/102 |
| 5,074,792 | 12/1991 | Bernadat ................................... 433/224 |
| 5,083,923 | 1/1992 | McSpadden .............................. 433/81 |
| 5,165,893 | 11/1992 | Thompson ................................ 433/81 |

FOREIGN PATENT DOCUMENTS

| | | | |
|---|---|---|---|
| 1271501 | 11/1986 | U.S.S.R. ................................ | 433/224 |
| 1304808 | 4/1987 | U.S.S.R. ................................ | 433/224 |

*Primary Examiner*—Cary E. O'Connor
*Attorney, Agent, or Firm*—Patula & Associates

[57] ABSTRACT

A hydraulic endodontia device and method comprised of a primary obturator rod having an objective tip end with at least one spill gate integrally formed therewithin and a handle end, the primary rod being generally cylindrical in shape and gradually diminishing in circumference from the handle end to said tip end. The invention is further defined by a plurality of secondary obturator rods each having an exterior convex side and an interior concave side. The interior concave side of each secondary rod glides upon the primary rod or the exterior convex side of an underlying secondary rod in cooperative association therewith when the open spill gate, the primary rod is inserted into the extirpated root canal until it reaches the distal end at the tip end, whereby narrowing of the distal root canal end constricts the spill gate to effuse cement to the apical area. Additional cement is applied to a plurality of secondary rod interior concave sides which are then inserted within the canal one rod at a time in cooperative association with the primary rod until complete obturation is achieved.

15 Claims, 2 Drawing Sheets

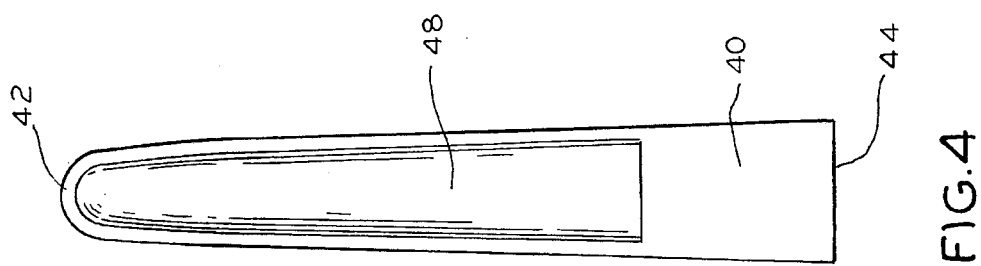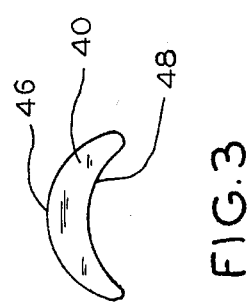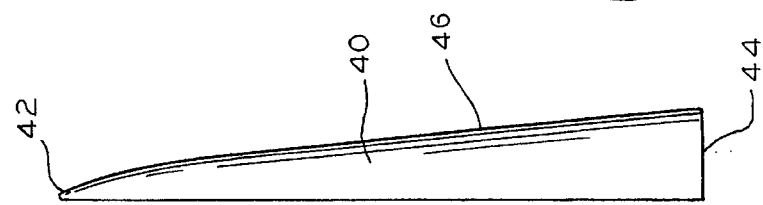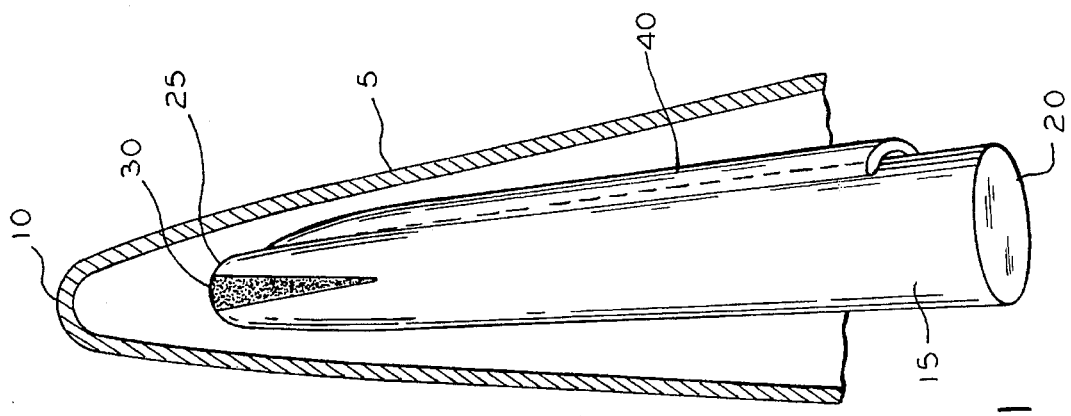

HYDRAULIC ENDODONTIA DEVICE

The present invention relates to endodontia instruments and, more particularly, to hydraulic instruments for use in root canal sealer placement.

BACKGROUND OF THE INVENTION

For the major part of this century, dentists and veterinarians have treated and saved teeth by transcoronal root canal obturation. Most have used plain round and tapered pure silver or gutta percha composite obturator rods to occlude the round apical or tip area of the tooth which is embedded in bone and tissue. Generally this involves somewhat haphazardous or blind insertion of a glue or cement into the extirpated root canal, followed by an obturator rod. Smaller round rods then are inserted into the canal around the first rod and used to occlude the remaining space in the ovoid sections.

A variety of endodontic instruments have been disclosed for improving root canal extirpation and obturation. U.S. Pat. No. 5,017,138, for example, teaches a set of improved cutting instruments for reaming, filing and shaping root canals in preparation for obturation. U.S. Pat. Nos. 4,518,356, 2,453,696 and 1,067,015 likewise disclose various instruments and designs for extirpating root canals. Other art has focused on obturation as well, such as in U.S. Pat. No. 5,083,923 in which an obturation method is recited as comprised of a combination of thermoplasticized gutta percha introduced into the bottom of the root canal, followed by a gutta percha point which then is manipulated within the canal to compact the thermoplasticized gutta percha and thereby fill the root canal with a core of filler material. U.S. Pat. No. 4,740,245 discloses a filling composition comprising a polymer component, a copolymer resin and an insoluble or sparingly soluble inorganic filler.

A critical problem with root canal obturation not addressed adequately by the prior art related to endodontia is that insertion of a rod or any material into a closed end channel can cause the entrapment of air at the distal end. This air can cause "interior ballistic ignition" and "blow back" of material and glue. At the least it can cause misapplication of material at a critical point and result in failure of treatment.

Current endodontia instruments and practices do not provide for carrying cement or glue to the distal (apical) areas with sufficient accuracy, or combat hydraulic pressure and material displacement blow back. Additionally, the presently manufactured secondary cones or rods used for filling or occluding the ovoid sections of a tooth canal are usually quite small to allow for negotiation of the small canal spaces. This creates a number of problems; namely, low tensile strength of such small rods as observed in U.S. Pat. No. 4,740,245, at lines 4–10, leading to filling difficulty. Also, because smaller rods are used, as many as 5 to 10 such rods are needed thereby requiring significant practitioner time and effort to complete filling.

One object of the present invention therefore is to provide an improved device for obturating an extirpated root canal which enhances distal apical performance of sealer placement.

Another object of the present invention is to improve the integrity of sealer placed within the extirpated root canal by eliminating or minimizing air pockets and blow back of sealer.

Another object of the present invention is to improve the strength of the secondary obturator rods by design features to allow for fewer rods to be used and, in turn, result in a more solid obturation.

Another object of the present invention is to diminish the effects of hydraulic and ballistic problems in root canal fill procedures by obturator rod feature designs.

Still another object of the present invention is to reduce obturation treatment time by improved obturator design features.

SUMMARY OF THE INVENTION

The present invention is comprised of a primary obturator rod having an objective tip end with a spill channel integrally formed therewithin and a handle end, said primary rod being generally cylindrical in shape and gradually diminishing in circumference from said handle end to said tip end. The invention is further defined by a plurality of secondary obturator rods having an exterior convex side and an interior concave side. The interior concave side of each secondary rod glides upon either the primary rod or the exterior convex side of an underlying secondary rod in cooperative association therewith when placed within the extirpated root canal for filling purposes.

Obturation sealer placement is effected using the present invention by inserting cementing glue within the spill gate of the primary rod of the invention upon opening it 10–15 degrees. The objective tip of the primary rod then is inserted into the extirpated root canal and the primary rod is slid down one side of the tooth chamber to protect the spill gate loaded material from drag on the other side of the tooth chamber. The spill gate constricts when the objective tip of the primary rod hits the narrower apical spaces, or from 2–5 millimeters from the very tip of the tooth, forcing material out against a circumference equal to the circumference of the objective tip. Air trapped in the distal extremity then is allowed to escape backward in a controlled manner through the velocity step design in the spill gate. Cement then is placed on the concave side of a secondary rod, which concave filled side is juxtaposed against the primary rod and slid longitudinally along it toward the apical canal end. Additional secondary rods are likewise loaded with cement along their respective interior concave sides and juxtaposed against either the primary rod or underlaying secondary rod exterior convex sides until the root canal is fully obturated.

Numerous other advantages and features of the invention will become readily apparent from the detailed description of the preferred embodiment of the invention, from the claims, and from the accompanying drawings, in which like numerals are employed to designate like parts throughout the same.

BRIEF DESCRIPTION OF THE DRAWINGS

A fuller understanding of the foregoing may be had by reference to the accompanying drawings, wherein:

FIG. 1 is a plain schematic view of a longitudinal cross-section of the endodontia device of the present invention showing the primary rod inserted within an extirpated root canal and a secondary rod juxtaposed against the primary rod.

FIG. 2 is a side view of a secondary rod of the present invention.

FIG. 3 is cross-sectional view of a secondary rod of the present invention.

FIG. 4 is a side elevational view of the concave face of a secondary rod showing a partial concave portion and a handle portion.

DETAILED DESCRIPTION OF THE INVENTION

Figure 9:
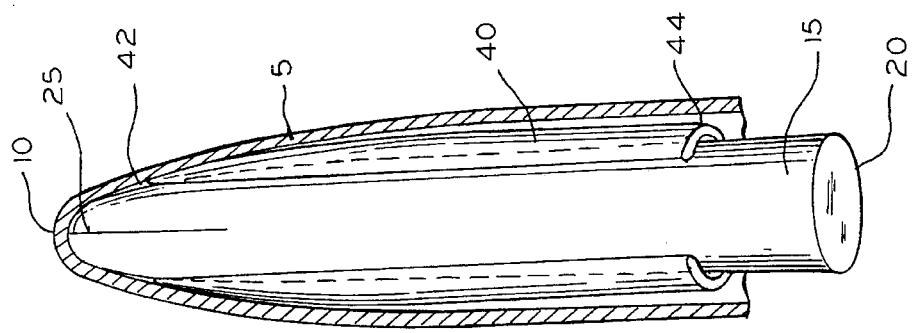
FIG. 9 is a longitudinal cross-sectional view of the present invention implanted within a fully obturated root canal.

While the invention is susceptible of embodiment in many different forms there is shown in the drawings, and will be described herein in detail, a preferred embodiment of the invention. It should be understood, however, that the present disclosure is to be considered an exemplification of the principles of the invention and is not intended to limit the spirit and scope of the invention and/or claims of the embodiment illustrated.

Figure 5:
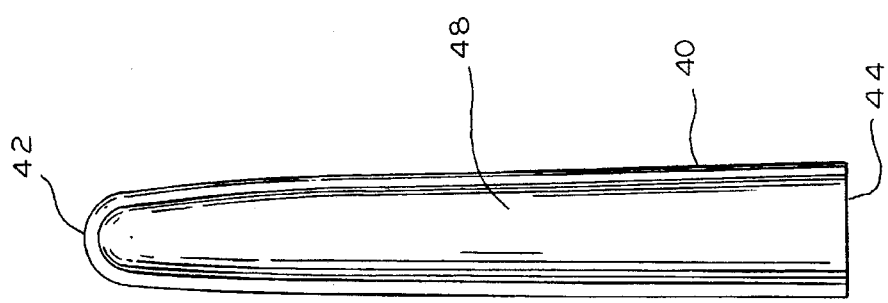
FIG. 5 is a side elevational view of the concave face of a secondary rod showing an alternate embodiment in which the concavity runs the full length of the rod.

Referring now to FIG. 1, the present invention is shown in cross-section as partially filling a root canal 5 having an apical end 10. The invention is comprised of a primary obturator cone or rod 15 having a handle end 20 and an objective tip end 25, said tip end 25 having a collapsible channel or spill gate 30 integrally formed therewithin. Primary rod 15 is generally cylindrical, calibrated to be of three degrees taper off central axis for approximately a 16 millimeter total length, the usual length of a human root canal, and diminishing gradually in circumference from said handle end 20 to said tip end 25. The present invention is further comprised of a plurality of secondary obturator cones or rods, one secondary rod 40 of which is depicted juxtaposed longitudinally along said primary rod 15 and a separate, side elevational view depicted in FIG. 2. Each said secondary rod 40 has an exterior convex side 46 of substantially the same degree, approximately three, of taper off central zero axis as primary rod 15. Each said secondary rod 40 is further defined by an interior concave side 48 which cooperatively associates with the exterior of primary rod 15 or exterior side 46 of an underlying secondary rod 40. Said interior concave side 48 may run the full length of secondary rod 40, as depicted in FIG. 5, or only a portion of its length, preferably three quarters, as depicted in FIG. 4.

FIG. 3 depicts a cross-sectional view of secondary rod 40 showing exterior convex side 46 and interior concave side 48. The one-half round tapered secondary rod 40 provides less impingement than full round cones when closing the remaining canal space most usually present in the ovoid section of a human root canal. Interior concave side 48 of secondary rod 40 serves as a tray for more additional viscous cement, as detailed below. Traditional cone-points do not offer such a feature even though additional cement normally is used in the finishing fill process. The edges of secondary rod 40 depicted in FIG. 3 as crescent tips may be rounded or feathered. In horizontal cross-section secondary rods 40 are diminishing in size by section from handle end 44 to tip end 42 in complementary degree with said primary rod from said handle end to said tip end.

Figure 6A:
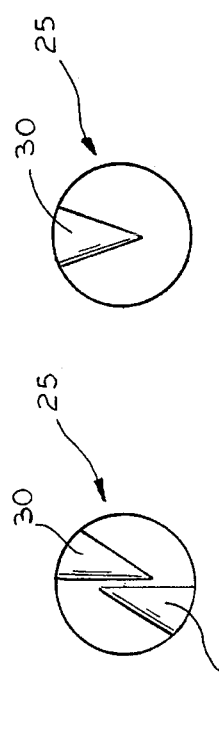
FIGS. 6a and 6b are top plan views of alternate embodiments of the objective tip end of the primary rod of the present invention.
Figure 6B:
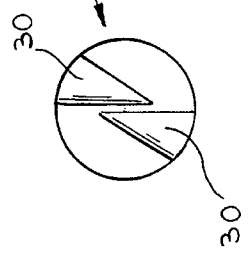

FIGS. 6a and 6b show said objective tip end 25 of primary rod 15 in alternate single spill gate and multiple spill gate embodiments, respectively. A plurality of spill gate channels of varying configurations is also possible, though not specifically depicted other than by FIG. 6b.

Figure 7:
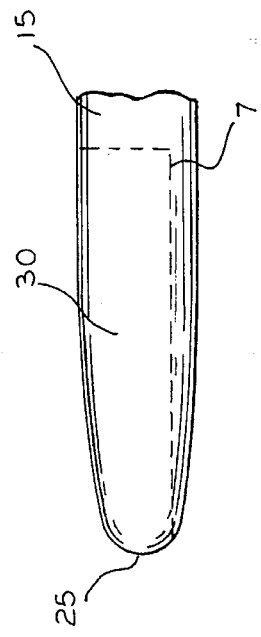
FIG. 7 is a partial side elevational view of the objective tip end of the primary rod of the present invention with phantom line representing the angle and depth of the tip end spill gate.
Figure 8:
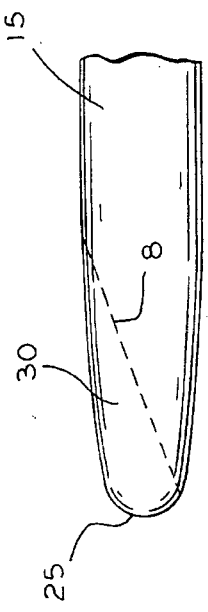
FIG. 8 is a partial side elevational view of the objective tip end of the primary rod of the present invention with phantom line representing an alternate embodiment angle of the tip end spill gate.

FIG. 7 shows said objective tip end 25 of primary rod 15. Phantom line 7 presents the depth and angle of cut of one embodiment said spill gate 30, the phantom line being the axis of spill gate 30. In an alternate embodiment as depicted in FIG. 8, the angle of cut of spill gate 30 is diagonal, as depicted by phantom line 8. In both embodiments, the spill gate cut ranges from five to ten millimeters in length. The descending radius of spill gate 30 gives it velocity reduction and compression capabilities when closing into distal (apical) region 10 upon forward constricting placement within canal 5.

The normal procedure for filling an extirpated root canal requires the insertion of obturation cement or glue in a blind fashion to the constricted distal apical tip portion. Lateral wall drag and air entrapment make the procedure uncertain as to final apication. The present invention ensures efficient final apication by loading viscous obturation cement into spill gate apex 30, which is open approximately one-third of the diameter of said objective tip end 25. Tip end 25 then is inserted into the extirpated root canal 5 and guided toward the distal apical end 10 shown in FIG. 1. As tip end 25 of primary rod 15 is urged into the narrower apical canal region 10, the spill gate 30 is forced to constrict, causing cement to effuse from the spill gate 30 into the apical end 10. Additional cement then is applied to interior side 48 of a secondary rod 40, with tip end 42 then inserted into the root canal 5 to juxtapose concave side 48 against primary rod 15. Tip end 42 guides upon primary rod 15 to slide secondary rod 40 along its length until tip end 42 reaches apical end 10, as depicted in FIG. 9. The procedure of filling interior concave side 48 of additional secondary rods 40 is repeated until complete obturation is achieved.

The foregoing specification describes only the preferred embodiment of the invention as shown. Other embodiments besides those shown in the drawings and described above may be articulated as well. The terms and expressions therefore serve only to describe the invention by example only and not to limit the invention. It is expected that others will perceive differences which while differing from the foregoing, do not depart from the spirit and scope of the invention herein described and claimed.

What I claim is:

1. A device for obturating an extirpated root canal, comprising:

a primary obturation rod having an objective tip with a collapsible spill gate cut into said objective tip, and a handle end; and a plurality of secondary obturation rods each having a tip end and a handle end adapted to cooperatively associate longitudinally with said primary obturation rod.

2. The device recited in claim 1, wherein said primary obturation rod is generally cylindrical and tapered at said objective tip end, and said secondary obturation rods are further each defined by a convex exterior side and a concave interior side of substantially the same arcuate degree as said primary obturation rod and adapted to be guided by said primary rod upon insertion within the extirpated root canal.

3. The device recited in claim 1, wherein said collapsible spill gate is comprised of channel walls which form a generally rectangular opening at said tip end prior to insertion within said root canal and forming essentially a right angle having its longitudinal leg approximately three degrees off zero relative to the central axis of said primary rod and its cross-sectional leg perpendicular thereto, said spill gate being approximately five to ten millimeters in length from said tip end.

4. The device recited in claim 1, wherein said collapsible spill gate is comprised of channel walls forming a diagonal cut from said tip end approximately three degrees off zero relative to the central axis of said primary rod, across said central axis, to the exterior of said primary rod for an approximate spill gate length of five to ten millimeters.

5. The device recited in claim 1, wherein each said secondary rod is tapered from said handle end to said tip end in degree complementary with said primary obturation rod.

6. The device recited in claim 1, wherein said secondary rods number between three and seven.

7. A device for obturating an extirpated root canal comprised of a cylindrical primary rod having a tip end and a handle end and gradually tapered from said handle end to said tip end, said tip end being further defined by at least one collapsible channel located at said tip end, said device further defined by a plurality of semi-cylindrical secondary rods each having a tip end and a handle end, a convex exterior side and a concave interior side adapted to cooperatively associate with said primary rod upon insertion within the extirpated root canal.

8. The device recited in claim 7, wherein said secondary rods each are tapered in complementary degree with said primary rod from said handle end to said tip end.

9. The device recited in claim 7, wherein said secondary rods number between three and seven.

10. A method for obturating an extirpated root canal having a distal portion, said method comprising the steps of:

inserting obturation cement into a collapsible mouth located at a tip end of a primary obturation rod;

inserting said primary rod into the extirpated root canal until said tip end juxtaposes the distal portion of said root canal;

urging closure of said collapsible mouth by exerting pressure on said primary rod against said distal end to cause effusion of obturation cement outside of the collapsed mouth and into the distal portion of the root canal;

applying obturation cement to a secondary obturation rod having a concave side and along said concave side;

inserting said secondary rod, further having a tip end and a handle end, into said root canal by guiding said concave side along the exterior of said primary rod until said tip end of said secondary rod reaches said distal portion of said root canal;

repeating application of obturation cement to concave sides of additional secondary rods and inserting said additional secondary rods within said root canal until said root canal is obturated fully.

11. The method recited in claim 10, wherein said step of repeating application of obturation cement to additional secondary rods and inserting within said root canal until said root canal is obturated fully is repeated two to six times.

12. A hydraulic endodontia device for obturating an extirpated root canal, comprising:

a primary obturator rod;

at least one spill gate in said primary obturator rod; and at least one secondary obturator rod;

said primary obturator rod and said at least one secondary obturator rods cooperating to obturate said extirpated root canal.

13. The device of claim 12, wherein said at least one secondary obturator rods includes a concave interior side portion.

14. The device of claim 13, wherein said at least one spill gate and said concave interior side portion receiving obturation cement.

15. The device of claim 12, wherein said at least one secondary obturator rods number three to seven.

\* \* \* \* \*